United States Patent [19]

Knebel et al.

[11] Patent Number: 5,567,826

[45] Date of Patent: Oct. 22, 1996

[54] PROCESS FOR THE PRODUCTION OF TERMINALLY NITROGEN HETEROCYCLE SUBSTITUTED (METH)ACRYLATE BY THE USE OF A MIXTURE OF AN ALKALI METAL AND ALKALINE EARTH METAL CATALYST

[75] Inventors: Joachim Knebel, Darmstadt; Peter J. Arndt, Seeheim-Jugenheim; Werner Ude, Darmstadt-Arheilgen, all of Germany

[73] Assignee: Roehm GmbH Chemische Fabrik, Darmstadt, Germany

[21] Appl. No.: 361,372

[22] Filed: Dec. 22, 1994

Related U.S. Application Data

[63] Continuation of Ser. No. 59,318, May 11, 1993, abandoned.

[30] Foreign Application Priority Data

May 23, 1992 [DE] Germany .......................... 42 17 124.5

[51] Int. Cl.$^6$ .................... C07D 233/32; C07D 247/02; C07D 239/10; C07D 243/04; C07D 245/02
[52] U.S. Cl. .................... 548/324.1; 540/460; 540/492; 544/318
[58] Field of Search .................... 548/324.1; 544/318; 540/460, 492

[56] References Cited

U.S. PATENT DOCUMENTS

| | | | |
|---|---|---|---|
| 2,871,223 | 1/1959 | Hankins et al. | 560/217 X |
| 3,940,415 | 2/1976 | Buchel et al. | 548/341.1 |
| 4,203,995 | 5/1980 | Funaki et al. | 548/341.1 X |
| 4,207,328 | 6/1980 | Kramer et al. | 548/341.1 X |
| 4,213,994 | 7/1980 | Gebbrt et al. | 548/341.1 X |
| 4,672,105 | 6/1987 | Schlosser et al. | 560/217 |
| 4,745,213 | 5/1988 | Schlosser et al. | 560/217 |

FOREIGN PATENT DOCUMENTS

| | | | |
|---|---|---|---|
| 0033501 | 8/1981 | European Pat. Off. | 548/341.1 |
| 0236994 | 9/1987 | European Pat. Off. | 560/217 |
| 0433135 | 6/1991 | European Pat. Off. | 560/217 |
| 0453638 | 10/1991 | European Pat. Off. | 560/217 |
| 0045600 | 5/1966 | Germany | 560/217 |
| 2656728 | 6/1978 | Germany | 548/341.1 |

*Primary Examiner*—Floyd D. Higel
*Attorney, Agent, or Firm*—Oblon, Spivak, McClelland, Maier, & Neustadt, P.C.

[57] ABSTRACT

Described is a process for producing (meth)acrylates with Formula (I)

$$\underset{H_2C=C-C-O-A-N}{\overset{R_1\ \ \ O}{|\ \ \ \ \ ||}}\!\!\diagup\!\!\overset{B}{\diagdown}\!\!\underset{\underset{O}{\overset{||}{C}}}{\diagdown}\!\!\diagup\!\!NH \quad (I)$$

with $R_1$ is H or $CH_3$, and A and B are each independently unbranched or branched alkylene groups with 2 to 5 C atoms, comprising the step of reacting a (meth)acrylate of the Formula (II), $$\underset{H_2C=C-C-O-R_2,}{\overset{R_1\ \ \ O}{|\ \ \ \ \ ||}} \quad (II)$$

wherein $R_2$ is alkyl especially with 1 to 4 C atoms and $R_1$ is as defined above, with an alcohol of the Formula (III)

$$HO-A-N\!\!\diagup\!\!\overset{B}{\diagdown}\!\!\underset{\underset{O}{\overset{||}{C}}}{\diagdown}\!\!\diagup\!\!NH, \quad (III)$$

wherein A and B are as defined above in the presence of an alkali earth catalyst or alkaline earth metal catalyst or a mixture thereof.

7 Claims, No Drawings

PROCESS FOR THE PRODUCTION OF TERMINALLY NITROGEN HETEROCYCLE SUBSTITUTED (METH)ACRYLATE BY THE USE OF A MIXTURE OF AN ALKALI METAL AND ALKALINE EARTH METAL CATALYST

This is a continuation of application Ser. No. 08/059,318 filed on May 11, 1993, now abandoned.

BACKGROUND OF THE INVENTION

1. Field of the Invention

This invention relates to a process for producing an acrylate or methacrylate of the formula:

$$H_2C=C(R_1)-C(=O)-O-A-N\underset{C(=O)}{\overset{B}{\diamond}}NH \quad (I)$$

wherein $R_1$ is hydrogen or a methyl group and A and B are each independently unbranched or branched alkylene groups with 2 to 5 carbon atoms.

2. Description of the Prior Art

Compounds of the Formula (I) may be obtained by the process of U.S. Pat. No. 2,871,223 by converting acrylic or methacrylic chloride with hydroxyalkyl-imidazolidin-2-ones in the presence of a tertiary nitrogen base, whereby a stoichiometric amount of the hydrochloride of the tertiary nitrogen base is also generated.

EP 0 236 994 A1 describes a process for producing an acrylate and methacrylate of the formula (I), by converting the acrylate or methacrylate with 1-(hydroxyalkyl)-imidazolidin-2-ones in the presence of either a titanium alcoholate or a titanium, zirconium, iron, or zinc chelating agent using 1,3-dicarbonyl compounds as a transesterification catalyst.

EP-A 0 433 135 and EP-A 0 453 638 describe the use of a diorganotinoxy compound as a transesterification catalyst for the conversion of an acrylate and methacrylate with a hydroxyalkyl imidazolidin-2-one into a compound of the formula In all these processes, the metal catalyst must be separated from the reaction mixture after conclusion of the conversion. When a tetraalkyl titanate or dialkyl tin oxide is used, the separation may be achieved by addition of water. Metal (hydro)oxides, such as $TiO_2$, may be produced from the corresponding titanate which can then be separated by filtering or centrifuging. Unfortunately, these hydrolyzed transesterification catalysts cannot be reused after separation. While dialkyl tin oxides can be separated and reused as transesterification catalysts; the separation step necessitates that a relatively large amount of water first be added and then removed from the reaction product.

DE-OS 34 23 441 and DE-OS 34 23 443 describe processes for producing esters using catalyst systems KS that are made up of lithium/calcium compounds.

SUMMARY OF THE INVENTION

It has now been found that the catalytic production of an acrylate or methacrylate of the formula (I) can be carried out by alcoholysis of an alkyl(meth)acrylate with an hydroxyalkyl-imidazolidin-2-one, using a catalyst which can be separated from the reaction mixture without the addition of water and which can be subsequently reused.

Accordingly, one object of this invention is to provide a novel process for producing an acrylate or methacrylate of the formula (I) from reactants (II) and (III) using a transesterification catalyst which can be readily separated from the reaction mixture without the necessity of first converting it to a separable form.

A second object of this invention is to provide a novel process for producing an acrylate or methacrylate of the formula (I) from reactants (II) and (III) using a transesterification catalyst which can be reused subsequent to removal from the reaction mixture without further workup.

It has now been found that the above conversion can be performed unexpectedly well with an alkali or alkaline earth metal compound used essentially as an oxide, hydroxide, carbonate, and/or as a salt of a carboxylic acid. Previously such compounds were known as esterification or transesterification catalysts to form alkyl(meth)acrylates. It was also known that these alkali/alkaline earth compounds could be separated from the reaction mixture without the addition of water. According to the present invention, a catalyst system KS consisting of the combination of compounds C and D has been found to be particularly advantageous, wherein C is a $Li_nY$, where Y is a halide, a chlorate, a carbonate or salt of a carboxylic acid with 1 to 6 carbon atoms, an alkoxide with 1 to 4 carbon atoms, hydroxide or oxygen, and n is either 1 or 2 corresponding to the valence of Y, D is $CaX_q$, wherein X is oxygen or chloride, and q is either 1 or 2 corresponding to the valence of X, provided that at least one of the two anionic components X and Y is oxygen.

These and other objects of the invention as will hereinafter be clarified, have been attained by a process of forming a compound of formula (I)

$$H_2C=C(R_1)-C(=O)-O-A-N\underset{C(=O)}{\overset{B}{\diamond}}NH \quad (I)$$

wherein $R_1$ is hydrogen or a methyl group, and A and B are each independently unbranched or branched alkylene groups with 2 to 5 C atoms, by transesterifying an acrylate or methacrylate of the Formula (II)

$$H_2C=C(R_1)-C(=O)-O-R_2, \quad (II)$$

wherein $R_1$ is as defined above and $R_2$ is an alkyl residue with 1 to 4 C atoms with a heterocyclic compound of the Formula (III)

$$HO-A-N\underset{C(=O)}{\overset{B}{\diamond}}NH, \quad (III)$$

wherein A and B are defined above, in the presence of an alkali/earth catalyst system.

The process is preferably performed using a catalyst system KS consisting of the combination of compounds C and D, wherein C and D are as defined above.

DETAILED DESCRIPTION OF THE PREFERRED EMBODIMENTS

In order to produce compounds of the Formula (I) according to the present invention, an acrylate or methacrylate of the Formula (II) where $R_2$ is an alkyl residue with 1 to 4 carbon atoms is used. Suitable compounds of the Formula (II) include: propyl acrylate, n-butyl acrylate, ethyl methacrylate, i-propyl methacrylate, i-butyl methacrylate, n-butyl methacrylate, and particularly methyl methacrylate.

Particularly suitable compounds of the Formula (III) include compounds in which A or B are each independently a branched or unbranched alkylene group with 2 to 5 carbon atoms, such as: $-(CH_2)_2-$, $-(CH_2)_3-$, $-(CH_2)_4-$, $-CH_2CH(CH_3)CH_2-$, and $-CH_2C(CH_3)_2CH_2-$. The heterocycle preferably contains 5 and 6 atoms. It is particularly advantageous to use, as compound (III), 1-(2-hydroxyethyl)-imidazolidin-2-one. 1-(2-hydroxyethyl)-imidazolidine-2-one can be produced according to U.S. Pat. No. 3,254,075 from aminoethyl ethanol amine and carbamide.

The catalyst or the catalyst system KS is used effectively in catalytic amounts, in general 0.01 to 5 w/w percent, preferably 0.05 to 1 w/w percent based on the total weight of reactants (II) and (III). A high selectivity of product (I) can be achieved when $R_1$ is $CH_3$ and A and B are each $-(CH_2)_2-$, and when 0.1 w/w percent, based on the total weight of methyl methacrylate and compound (III), of catalyst system KS is used, preferably when catalyst system KS is a LiOH/CaO mixture. The content of component C in the catalyst system KS (consisting of C and D) is 5 to 95 w/w percent, preferably 90 to 10 w/w percent; and the content of component D is 95 to 5 w/w percent, preferably 90 to 10 w/w percent. In particular, the weight of D is present in an excess to the weight of C, preferably the weight of D is at least double the weight of C.

The catalyst is preferably used as a finely divided powder or crystal. Components C and D may be admixed prior to use, but alternatively may be added to the reaction batch as individual components.

Suitable catalyst systems KS are:

lithium oxide and calcium oxide, lithium hydroxide and calcium oxide, lithium alkoxide and calcium oxide, lithium carbonate and calcium oxide, lithium acetate and calcium oxide, lithium fluoride and calcium oxide, lithium chloride and calcium oxide, lithium bromide and calcium oxide, lithium iodide and calcium oxide, lithium chlorate and calcium oxide, and lithium methylate and calcium chloride. Alkoxides, such as methoxides, ethoxides, or tertiary butoxides are particularly preferred.

The conversion (alcoholysis) of the Formula (II) acrylate and/or methacrylate to a Formula (III) alcohol is preferably performed at a temperature of between 30 and 180° C., especially between 50 and 130° C., in the presence of 0.01 to 10 w/w percent catalyst system KS relative to the weight of the reaction mixture.

Equimolar amounts of reactants (II) and (III) are reacted by forming the desired end products (I). In practice, it is preferable to always use an excess of starting esters (II) during the conversion. Compound (II) is used in amounts from 1 to 20, preferably 2 to 10, especially 3 to 6 mol per mol of compound (III).

In order to avoid side products produced by polymerization, it is useful to perform the conversion and processing of the reaction mixture in the presence of polymerization inhibitors such as phenothiazine, hydroquinone monomethyl ether, and particularly oxygen.

The conversion may take place under normal, reduced or excessive pressure. It may take place discontinuously or continuously. Starting compounds (II) and (III) are, for example, heated together to their boiling points in the presence of the catalyst system consisting of alkali and/or earth alkali compounds, especially the catalyst system KS consisting of components C and/or D. Following conversion, the alcohol $R_2OH$, possibly in the form of its azeotrope, is distilled off. After conclusion of the conversion, excess monomer ester (II) can also be removed completely or partially by distillation. Depending on the reaction temperature, catalyst, or catalyst amount, the reaction times range from approximately 1 to 7 hours. It is also possible to perform the process of the present invention in the presence of an inert solvent such as toluene or cyclohexane.

The dispersed catalyst can be removed by filtering, preferably prior to the distillation of excess monomer ester (II). However, is also is possible to perform the separation after partial or complete removal of excess monomer ester (II). The catalyst system KS that has been recovered in filtered-off form may then be reused, either directly or after drying.

A preferred conversion product is one that consists of methyl methacrylate and 1-(2-hydroxyethyl)-imidazolidin-2-one, and thus corresponds to Formula (I) with $R_1=CH_3$, $A=-(CH_2)_2$, —and $B=-(CH_2)_2-$.

A particular advantage of the present invention is that the catalyst is suspended virtually quantitatively in the reaction mixture and can be separated without adding water and without physical separation aids, such as filtration, and further can be reused.

Compounds of the Formula (I) are valuable comonomers and are useful in the production of polymer dispersions of vinyl monomers that are used primarily as binders, such as in lacquers, or as leather aids. Comonomers of the Formula (I) provide copolymers with a high degree of hydrophilicity, and which when used to produce thermally hardenable resins are able to function as formaldehyde scavengers due to their imide groups.

The selectivity provided by the process of the present invention is surprising, since the bifunctionalities of compounds (I) and (II) would be expected to undergo side reactions, such as addition reactions analogous to Michael addition to the double bond, or amide formation due to reaction of the acrylate or methacrylate (I) with the NH group of a compound (II) in the presence of the relatively strong basic catalyst components. However, the process of the present invention transesterifies acrylates and methacrylates of the Formula (II) and alcohols of the Formula (III) extremely selectively into compounds of the Formula (I). Compared to previous precesses which used dibutyl tin oxide as a catalyst, the reaction time of the present invention is reduced by approximately 50%, and the amount of catalyst necessary for conversion has been reduced by a factor 10.

The present invention produces compounds of the Formula (I) that can be used without further costly and qualitatively unfavorable separation processes. These compounds can be used directly as copolymers, especially in the production of dispersion polymers. Further, these compounds do not contain any heavy metal components used in the production. Compounds (I) can also be produced as solid products according to this process, for example, by concentrating the solution.

Having generally described this invention, a further understanding can be obtained by reference to certain specific examples which are provided herein for purposes of illustration only and are not intended to be limiting unless otherwise specified.

EXAMPLES

Example 1

248 g of 1-(2-hydroxyethyl)-imidazolidin-2-one (also called N-(hydroxyethyl)ethylene carbamide) and 1,050 g methyl methacrylate (MMA) were placed in a 2L round-bottom four-neck flask with attached column and reflux condensor. For stabilization, 500 ppm p-methoxyphenol and 50 ppm phenothiazine were added, and air was passed in a slow stream through the reaction mixture during the transesterification. First, the batch was dehydrated, with the reflux condensor open, by drawing off the MMA-water azeotrope until a head temperature of 99° C. was established. Cooling to 70 to 85° C. (bottom temperature) followed, and a pulverized catalyst comprising 0.94 g calcium oxide and 0.36 g lithium hydroxide which had been suspended in MMA (in amounts corresponding to the previously withdrawn azeotrope) was added.

Then the alcoholysis was performed at a bottom temperature of 95 to 102° C. and a head temperature of 64 to 70° C., whereby the methanol-MMA azeotrope was removed with a reflux ratio of 5:1 to 5:2. After 1 to 2 hours, a conversion of 95% was achieved (determined via the methanol amount), and the reaction was stopped. The reaction mixture was cooled, the catalyst was separated from the reaction mixture by filtration, and the filtrate was analyzed using gas chromatography (GC):

PRODUCT COMPOSITION

MMA: 67%

N-(methacryloyl oxyethyl) ethylene carbamide: 21.6%

N-(hydroxyethyl) ethylene carbamide: 4.8%

N-(methacryloyl oxyethyl)-N'-(methacryloyl) ethylene carbamide: 1.7%

N-(methacryloyl oxyethyl)-N'-(2-(methoxycarbonyl)propyl)ethylene carbamide: 0.6%.

Example 2

248 g of 1-(2-hydroxyethyl)-imidazolidin-2-one and 1,050 g methylmethacrylate were subjected to the process of Example 1, with the exception that a mixture of 0.65 g lithium chloride and 0.65 g calcium oxide was used as catalyst. According to GC, the filtered reaction mixture had the following composition:

PRODUCT COMPOSITION

MMA: 68.2%

N-(methacryloyl oxyethyl) ethylene carbamide: 21.8%

N-(hydroxyethyl) ethylene carbamide: 4.8%

N-(methacryloyl oxyethyl)-N'-(methacryloyl) ethylene carbamide: 17%

N-(methacryloyl oxyethyl)-N'-(2-(methoxycarbonyl)propyl) ethylene carbamide: 0.5%.

Example 3

248 g of 1-(2-hydroxyethyl)-imidazolidin-2-one and 1,050 g methylmethacrylate were subjected to the process of Example 1, with the exception that 280 ppm (related to total weight) of lithium hydroxide were used as catalyst. According to GC, the filtered reaction mixture had the following composition:

PRODUCT COMPOSITION

MMA: 67.7%

N-(methacryloyl oxyethyl) ethylene carbamide: 23%

N-(hydroxyethyl) ethylene carbamide: 4.3%

N-methacryloyl oxyethyl)-N'-(methacryloyl) ethylene carbamide: 1.6%

N-(methacryloyl oxyethyl)-N'-(2-(methoxycarbonyl)propyl) ethylene carbamide: 0.6%

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing a (meth) acrylate of the Formula

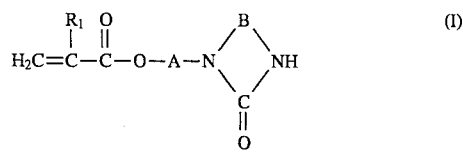

wherein $R_1$ is hydrogen or methyl, and A and B are each independently unbranched or branched alkylene groups of 2 to 5 C atoms, which comprises reacting an acrylate or methacrylate of the Formula (II)

where $R_1$ is defined as above and $R_2$ is alkyl with 1 to 4 C atoms, with a heterocyclic compound of the Formula (III)

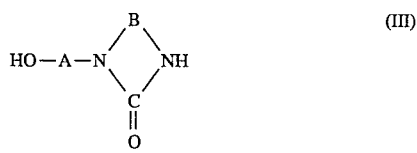

wherein the reaction is performed in the presence of a 0.01 to 0.1 wt. % of a mixture of an alkali metal catalyst and an alkaline earth metal catalyst, wherein the amount of alkali metal catalyst is 5 to 95 w/w percent and the amount of alkaline earth metal catalyst is 95 to 5 w/w based on the total amount of alkali metal and alkaline earth metal catalysts.

2. The process according to claim 1, wherein the catalyst is a catalyst system comprising a mixture of lithium and calcium compounds.

3. The process according to claim 1, wherein the catalyst is a catalyst system comprising C and D:
wherein C is $Li_nY$, where Y is a halide, a chlorate, a carbonate or salt of a carboxylic acid with 1 to 6 carbon atoms, an alkoxide with 1 to 4 carbon atoms, hydroxide, or oxygen, and n is either 1 or 2 corresponding to the valence of Y, and D is $CaX_q$, where X is oxygen or chloride, and q is either 1 or 2 corresponding to the valence of X, provided that at least one of the two anionic components X and Y contains oxygen.

4. The process according to claim 3, wherein the amount of compound C in catalyst system is 5 to 95 w/w percent and that of compound D is 95 to 5 w/w percent.

5. The process according to claim 3, wherein the catalyst is a catalyst system selected from the group consisting of:

calcium oxide and lithium oxide, calcium oxide and lithium hydroxide, calcium oxide and lithium methylate, calcium oxide and lithium t-butoxide, calcium oxide and lithium acetate,
calcium oxide and lithium chloride,
calcium oxide and lithium bromide,
calcium oxide and lithium iodide,
calcium oxide and lithium chlorate, and
calcium chloride and lithium methylate.

6. The process according to claim 1, wherein the compound of the Formula (I) is 1-(2-hydroxyethyl)-imidazolidin-2-one.

7. The process according to claim 1, wherein the compound of the Formula (II) is methyl methacrylate.

* * * * *